United States Patent [19]

Anatol, deceased et al.

[11] 4,376,783

[45] Mar. 15, 1983

[54] ACYLATED GUANIDINES AND MEDICAMENTS CONTAINING THEM

[75] Inventors: Jesus Anatol, deceased, late of Paris, France; by Marie-Francoise Anatol, legal representative; by Andre-Manuel Anatol, legal representative, both of Seine, France; Jean Berecoechea, Reims, France; Pierre Duchene-Marullaz, Chamalieres, France; Alain Eschalier, Clermont-Ferrand, France

[73] Assignee: Compagnie Francaise de Sucerie, Paris, France

[21] Appl. No.: 240,512

[22] Filed: Mar. 4, 1981

[30] Foreign Application Priority Data

Mar. 7, 1980 [FR] France ................ 80 05190

[51] Int. Cl.³ .................. A61K 31/27; A61K 31/165; C07C 103/78; C07C 125/063

[52] U.S. Cl. ...................... 424/300; 560/27; 560/28; 560/29; 564/47; 564/48; 564/56; 564/185; 424/322; 424/324

[58] Field of Search ............. 564/52, 47, 185, 237, 564/239; 424/322, 326, 300, 324; 560/34, 27, 28, 29

[56] References Cited

U.S. PATENT DOCUMENTS 3,437,691  4/1969  Faith .................... 564/237
3,542,873  11/1970  Faith .................... 424/326
3,873,600  3/1975  Brandstrom et al. ........ 560/29
4,010,189  3/1977  Smith .................... 560/29

Primary Examiner—Natalie Trousof
Assistant Examiner—L. Hendriksen
Attorney, Agent, or Firm—Karl W. Flocks; Sheridan Neimark

[57] ABSTRACT

The novel acylated guanidines, ureas and substituted ureas correspond to the general formula:

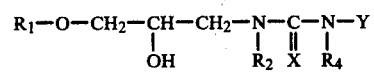

$$R_1-O-CH_2-CH-CH_2-N-C-N-Y$$
$$\phantom{R_1-O-CH_2-}|\phantom{CH-CH_2-}|\phantom{C-}\|\phantom{-}|$$
$$\phantom{R_1-O-CH_2-}OH\phantom{CH-CH_2-}R_2\phantom{}X\phantom{}R_4$$

in which $R_1$ repesents a substituted or unsubstituted aromatic ring, $R_2$ represents an alkyl, aryl, or arylalkyl group, $R_4$ repesents hydrogen or a variously substituted aryl group, X is oxygen or an imine group: NH and Y represent an alkyl aryl alkyloxy or aryloxy group or a hydrogen atom when X represents oxygen or the group $COR_3$ with $R_3$ representing an aromatic group, an aryloxy, aralkyloxy or alkyloxy group when X represents the NH group. They are prepared by heating an appropriate compound under reflux with an oxyaminoalcohol, in a suitable solvent. The products are useful as medicaments for the treatment of arterial hypertension, ischemica diseases of the heart and rhythmic disorders of the latter.

4 Claims, No Drawings

ACYLATED GUANIDINES AND MEDICAMENTS CONTAINING THEM

The present invention relates to novel acylated guanidines, ureas and substituted ureas corresponding to the general formula:

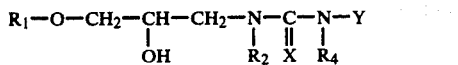
(I)

in which $R_1$ represents a substituted or unsubstituted aromatic ring, $R_2$ represents an alkyl, aryl, arylalkyl or cycloalkyl group, $R_4$ represents hydrogen or a variously substituted aryl group, X is oxygen or an imine group: NH and Y represents an alkyl, aryl, alkyloxy or aryloxy group or a hydrogen atom when X represents oxygen or the group $COR_3$ with $R_3$ representing an aromatic group, an aryloxy group, aralkyloxy or alkyloxy group when X represents the NH group.

The invention is also directed to a process for preparing these novel compounds. This process consists of reacting an oxyaminoalcohol of the formula:

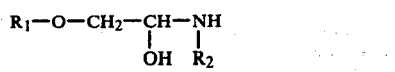
(II)

where $R_1$ and $R_2$ have the above meanings with a compound of the formula:

(III)

where X and Y have the above meaning, by simple heating under reflux in the presence of a suitable solvent.

By proceding in this manner, it is possible to obtain, according to the invention, compounds corresponding to the general formula (I) of the series of guanidines corresponding more specifically to the formula:

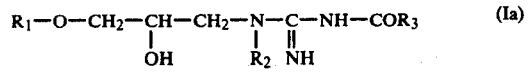
(Ia)

when the compound of formula (III) is a cyanamide

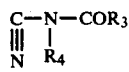

according to the equation:

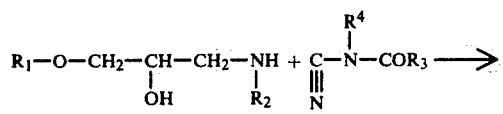

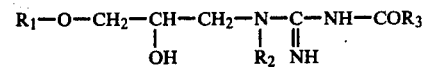

or compounds corresponding to the general formula (I) of the series of ureas and substituted ureas corresponding more specifically to the formula:

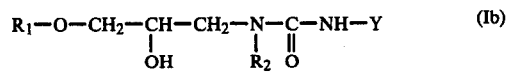
(Ib)

when the compound of formula (III) is an isocyanate

according to the equation:

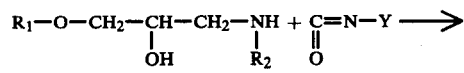

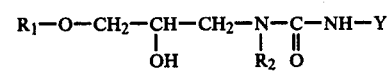

or again, in the case where Y represents hydrogen, compounds:

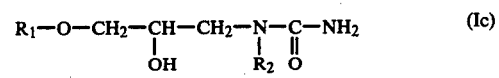
(Ic)

The following Examples are given by way of illustration of the invention and are to be taken as in no way limiting.

EXAMPLE 1

1-(3-methyl-1-phenyloxy, 2 hydroxy propyl), 1-cyclohexyl 3- benzoyl guanidine-Compound SCS 300

In a round flask fitted with an overhead condenser, 13.5 g (0.05 mole) of (3-methyl 1-phenyloxy 2-hydroxy propyl)-cyclohexylamine are dissolved in 50 ml of ethanol. 7.2 g (0.05 mole) of benzoylcyanamide dissolved in 20 ml of ethanol was added. It was heated under reflux for 16 hours. The ethanol was evaporated under reduced pressure. The residual oil was recrystallized in a mixture of ethyl acetate and isopropyl oxide. A product melting at 105° C. was obtained.

Analysis: $C_{24}H_{31}O_3N_3$; M.W.=409,51. calculated: C, 70.39; H, 7.63; N, 10.26. found: C, 70.58; H, 7.83; N, 9.90.

Table I below gives the results obtained by applying the same process, the products all corresponding to the formula shown at the head of this Table.

TABLE I $$R_1-O-CH_2-CH(OH)-CH_2-N(R_2)-C(=NH)-NH-Y$$

| Reference product SCS | $R_1$ | $R_2$ | Y | Recrystallization solvent | M.P. °C. | ANALYSIS | | |
|---|---|---|---|---|---|---|---|---|
| | | | | | | C | H | N |
| 149 | 2-CH₃-C₆H₄- | (CH₃)₂-CH- | C₆H₅-CO- | AcOEt + Isop. oxide | 81 | Calcul.: 68.26<br>Found: 68.09 | 7.36<br>7.39 | 11.31<br>11.10 |
| 150 | 2-CH₃-C₆H₄- | (CH₃)₂CH- | C₂H₅-O-CO- | AcOEt | 105 | Calcul.: 60.51<br>Found: 60.54 | 8.06<br>8.11 | 12.45<br>12.59 |
| 295 | 2-CH₃-C₆H₄- | C₆H₁₁- | C₆H₅-CO- | AcOEt + Isop. oxide | 92 | Calcul.: 70.38<br>Found: 70.37 | 7.63<br>7.66 | 10.26<br>10.03 |
| 151 | 2-CH₃-C₆H₄- | C₆H₁₁- | C₂H₅-O(CO- | AcOEt + Isop. oxide | 104 | Calcul.: 63.63<br>Found: 63.53 | 8.28<br>8.35 | 11.13<br>11.10 |
| 296 | 2-CH₃-C₆H₄- | C₆H₅-CH₂- | C₂H₅-O-CO- | AcOEt | 88 | Calcul.: 65.43<br>Found: 65.48 | 7.06<br>7.16 | 10.90<br>10.93 |
| 297 | 2-CH₃-C₆H₄- | CH₃-(CH₂)₃- | C₂H₅-O-CO- | AcOEt + Isop. oxide | | Calcul.: 61.52<br>Found: 61.65 | 8.32<br>8.42 | 11.96<br>11.93 |
| 298 | 2-CH₃-C₆H₄- | C₆H₁₁- | C₆H₅-CH₂-O-CO- | AcOEt or EtOH + H₂O | 90 | Calcul.: 68.31<br>Found: 68.12 | 7.57<br>7.50 | 9.56<br>9.63 |
| 299 | 2-CH₃-C₆H₄- | H | C₆H₅-CO- (bis) | EtOH + H₂O | | Calcul.: 66.03<br>Found: 66.00 | 6.47<br>6.80 | 12.84<br>12.93 |
| 300 | 3-CH₃-C₆H₄- | C₆H₁₁ | C₆H₅-CO- | AcOEt + Isop. oxide | 105 | Calcul.: 70.39<br>Found: 70.58 | 7.63<br>7.83 | 10.16<br>9.90 |
| 152 | 2-Cl-3-CH₃-C₆H₃- | (CH₃)₂-CH- | C₂H₅-O-CO- | AcOEt | 110 | Calcul.: 60.51<br>Found: 60.61 | 8.07<br>8.12 | 12.45<br>12.48 |
| 146 | 2-Cl-C₆H₄- | C₆H₁₁- | C₂H₅-O-CO- | AcOEt + Isop. oxide | 100 | Calcul.: 57.34<br>Found: 57.45 | 7.09<br>7.15 | 10.56<br>10.46 |
| 145 | 2-Cl-C₆H₄- | C₆H₁₁- | C₆H₅-CO- | AcOEt + Hexane | 114 | Calcul.: 64.24<br>Found: 64.24 | 6.56<br>6.59 | 9.77<br>9.85 |
| 148 | 4-Cl-C₆H₄- | (CH₃)₂CH- | C₂H₅-O-CO- | AcOEt + Isop. oxide | 86 | Calcul.: 53.69<br>Found: 53.75 | 6.76<br>6.80 | 11.74<br>11.68 |
| 301 | 4-Cl-C₆H₄- | C₆H₁₁ | C₆H₅-CO- | AcOEt + Hexane | 118 | Calcul.: 64.24<br>Found: 63.86 | 6.56<br>6.58 | 9.77<br>9.50 |

TABLE I-continued $$R_1-O-CH_2-CH(OH)-CH_2-N(R_2)-C(=NH)-NH-Y$$

| Reference product SCS | $R_1$ | $R_2$ | Y | Recrystallization solvent | M.P. °C | ANALYSIS | | |
|---|---|---|---|---|---|---|---|---|
| | | | | | | | C | H | N |
| 147 | Cl—C$_6$H$_4$— | C$_6$H$_{11}$ | C$_2$H$_5$—O—CO— | EtOH + Isop. oxide | 132 | Calcul.: | 57.34 | 7.09 | 10.56 |
| | | | | | | Found: | 57.41 | 7.05 | 10.52 |
| 144 | methylnaphthyl | C$_6$H$_{11}$ | C$_6$H$_5$—CO— | AcOEt + Hexane | 120 | Calcul.: | 72.78 | 7.01 | 9.43 |
| | | | | | | Found: | 72.68 | 6.95 | 9.48 |

EXAMPLE 2

1-(2-methyl 1-phenyloxy, 2-hydroxy propyl) 1-cyclohexyl 3-phenyl urea-Product SCS 303

5.26 g (0.02 mole) of (2-methyl 1-phenyloxy 2-hydroxy propyl)-cyclohexylamine is dissolved in 300 ml of benzene. 2.38 g (0.02 mole) of phenylisocyanate were added. Slight heating was observed as well as the appearance of a solid. It was heated under reflux for 1 hour. After cooling, it was filtered and the product was recrystallized in ethanol. Melting point 164° C.

Analysis: $C_{23}H_{30}N_2O_3$; M.W.=382.49. calculated: C, 72.22; H, 7.90; N, 7.32. found: C, 72.14; H, 7.86; N, 7.38.

Table II below gives the results obtained by applying the same process, the products all corresponding to the formula shown at the head of this Table.

TABLE II $$R_1-O-CH_2-CH(OH)-CH_2-N(R_2)-CO-NH-Y$$

| Reference product SCS | $R_1$ | $R_2$ | Y | Recrystallization solvent | M.P. °C | ANALYSIS | | | |
|---|---|---|---|---|---|---|---|---|---|
| | | | | | | | C | H | N |
| 302 | 2-methylphenyl | (CH$_3$)$_2$—CH | phenyl | EtOH + H$_2$O | 165 | Calcul.: | 70.15 | 7.65 | 8.18 |
| | | | | | | Found: | 70.18 | 7.65 | 8.28 |
| 303 | 2-methylphenyl | C$_6$H$_{11}$ | phenyl | EtOH | 164 | Calcul.: | 72.22 | 7.90 | 7.32 |
| | | | | | | Found: | 72.14 | 7.86 | 7.38 |
| 304 | 2-methylphenyl | CH$_3$—(CH$_2$)$_5$— | phenyl | EtOH + H$_2$O | 120 | Calcul.: | 70.76 | 7.92 | 7.86 |
| | | | | | | Found: | 70.88 | 7.87 | 8.02 |
| 305 | 2-chlorophenyl | C$_6$H$_{11}$ | phenyl | EtOH | 170 | Calcul.: | 65.57 | 6.75 | 6.95 |
| | | | | | | Found: | 65.42 | 6.76 | 7.02 |
| 306 | 4-chlorophenyl | (CH$_3$)$_2$—CH— | phenyl | EtOH | 152 | Calcul.: | 62.88 | 6.39 | 7.72 |
| | | | | | | Found: | 62.87 | 6.34 | 7.80 |
| 126 | 4-chlorophenyl | (CH$_3$)$_2$—CH— | —(CH$_2$)$_3$—CH$_3$ | AcOEt + Petrol ether. | 100 | Calcul.: | 59.50 | 7.88 | 7.80 |
| | | | | | | Found: | 59.40 | 7.89 | 8.08 |
| 307 | methylnaphthyl | C$_6$H$_{11}$ | phenyl | EtOH + Petrol ether | 150 | Calcul.: | 74.61 | 7.22 | 6.69 |
| | | | | | | Found: | 74.31 | 7.13 | 6.68 |
| 308 | methylnaphthyl | (CH$_3$)$_2$—CH— | phenyl | AcOEt | 158 | Calcul.: | 72.99 | 6.92 | 7.40 |
| | | | | | | Found: | 72.95 | 6.84 | 7.45 |
| 127 | 4-methylphenyl | (CH$_3$)$_2$—CH— | —(CH$_2$)$_3$—CH$_3$ | AcOEt + Petrol ether | 92 | Calcul.: | 67.04 | 9.38 | 8.69 |
| | | | | | | Found: | 67.05 | 9.37 | 8.78 |

TABLE II-continued $$R_1-O-CH_2-CH(OH)-CH_2-N(R_2)-CO-NH-Y$$

| Reference product SCS | $R_1$ | $R_2$ | Y | Recrystallization solvent | M.P. °C. | ANALYSIS | | |
|---|---|---|---|---|---|---|---|---|
| | | | | | | C | H | N |
| 128 | 2-methylnaphthyl | $(CH_3)_2-CH-$ | $-(CH_2)_3-CH_3$ | AcOEt + Petrol ether | 110 | Calcul.: 70.36<br>Found: 70.28 | 8.44<br>8.44 | 7.81<br>7.87 |

EXAMPLE 3

1-(2-Chloro 1-phenyloxy 2-hydroxy propyl) 1-isopropyl urea Product SCS 313

2.8 g (0.01 mole) of (2-chloro 1-phenyloxy, 2-hydroxy propyl)-isopropylammonium chloride was dissolved in 20 ml of water and 5 ml of ethanol. 0.97 g (0.012 mole) of potassium cyanate was added. It was left to stand for 16 hours. It was filtered and recrystallized from a mixture of water and ethanol. A product melting at 154° C. was obtained.

Analysis: $C_{13}H_{19}ClN_2O_3$; M.W.=286.80. Calculated: C, 54.44; H, 6.68; N, 9.77. Found: C, 54.41; H, 6.70; N, 9.73.

Table III below gives the results obtained by applying the same process, the products all corresponding to the formula shown at the head of this Table.

TABLE III $$R_1-O-CH_2-CH(OH)-CH_2-N(R_2)-CONH_2$$

| Reference product SCS | $R_1$ | $R_2$ | Recrystallization solvent | M.P. °C. | ANALYSIS | | |
|---|---|---|---|---|---|---|---|
| | | | | | C | H | N |
| 309 | 2-methylphenyl | $(CH_3)_2-CH-$ | EtOH + $H_2O$ | 150 | Calcul.: 63.13<br>Found: 63.08 | 8.33<br>8.34 | 10.52<br>10.50 |
| 310 | 2-methylphenyl | $(CH_3)_3-C-$ | EtOH | 150 | Calcul.: 64.26<br>Found: 64.19 | 8.63<br>8.49 | 9.99<br>9.96 |
| 311 | 2-methylphenyl | $C_6H_{11}-$ | EtOH + $H_2O$ | 170 | Calcul.: 66.64<br>Found: 66.55 | 8.55<br>8.64 | 9.14<br>9.28 |
| 312 | 3-methylphenyl | $(CH_3)_2-CH-$ | EtOH + $H_2O$ | 130 | Calcul.: 63.13<br>Found: 63.26 | 8.33<br>8.43 | 10.52<br>10.42 |
| 313 | 2-chlorophenyl | $(CH_3)_2-CH-$ | EtOH + $H_2O$ | 154 | Calcul.: 54.44<br>Found: 54.51 | 6.68<br>6.70 | 9.77<br>9.73 |
| 314 | 2-chlorophenyl | $CH_3-(CH_2)_3-$ | EtOH + $H_2O$ | 110 | Calcul.: 55.89<br>Found: 55.84 | 7.04<br>6.95 | 9.31<br>9.05 |
| 315 | 2-chlorophenyl | $C_6H_{11}-$ | EtOH | 176 | Calcul.: 58.79<br>Found: 58.80 | 7.09<br>7.02 | 8.57<br>8.47 |
| 129 | 4-chlorophenyl | $(CH_3)_2-CH-$ | EtOH | 146 | Calcul.: 54.44<br>Found: 54.22 | 6.63<br>6.63 | 9.77<br>9.55 |
| 316 | 4-chlorophenyl | $CH_3-(CH_2)_3-$ | AcOEt + Isop. oxide | 90 | Calcul.: 55.89<br>Found: 55.74 | 7.04<br>6.97 | 9.31<br>9.12 |

(bis)

TABLE III-continued $$R_1-O-CH_2-CH(OH)-CH_2-N(R_2)-CONH_2$$

| Reference product SCS | $R_1$ | $R_2$ | Recrystallization solvent | M.P. °C. | ANALYSIS | | |
|---|---|---|---|---|---|---|---|
| | | | | | C | H | N |
| 317 |  Cl-C6H4- | $C_6H_{11}$ | EtOH | 158 | Calcul.: 58.79<br>Found: 58.61 | 7.09<br>7.01 | 8.57<br>8.32 |
| 318 |  Cl-C6H4- | 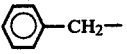 C6H5-CH2- | EtOH + Isop. oxide | 126 | Calcul.: 60.97<br>Found: 60.92 | 5.72<br>5.63 | 8.37<br>8.20 |
| 131 |  naphthyl | $(CH_3)_2-CH-$ | EtOH | 152 | Calcul.: 67.52<br>Found: 67.64 | 7.33<br>7.34 | 9.26<br>9.31 |
| 319 |  naphthyl | $CH_3-(CH_2)_3-$ | EtOH + $H_2O$ | 126 | Calcul.: 68.33<br>Found: 68.41 | 7.65<br>7.54 | 8.85<br>8.73 |
| 320 |  naphthyl | $C_6H_{11}$ | EtOH + $H_2O$ | 206 | Calcul.: 70.15<br>Found: 70.09 | 7.65<br>7.73 | 8.18<br>8.23 |
| 130 |  CH3-C6H4- | $(CH_3)_2-CH-$ | EtOH + $H_2O$ | 160 | Calcul.: 63.13<br>Found: 62.96 | 8.33<br>8.46 | 10.52<br>10.59 |

The compounds of the invention besides being interesting in industrial chemical synthesis operations, find application, according to their molecular structure, in various fields such as those of agriculture, the pharmaceutical industry, etc.

Thus it can be indicated notably that compounds such as SCS and 149 and 150 gave beta-blocking effects, that the compounds such as SCS 146, 147, 148 151 have sympathomimetic action and that the compounds SCS 128 and 131 have cardiac stimulant effects making them interesting in the field of therapeutics.

Tests carried out, taking as an element for comparison, Pindolol, which is, of all the beta-blocking agents currently used in therapeutics, that whose intrinsic sympathomimetic action is greatest, have shown that:

the compound SCS 146 possesses considerable sympathomimetic activity;

the compound SCS 147 possesses such sympathomimetic activity still greater than that of the preceding compound;

that the compound SCS 148 possesses a certain beta-blocking action masked by intrinsic sympathomimetic properties;

that the compound SCS 149 possesses undisputable beta-blocking properties (about 60% of the beta-blocking properties of Pindolol) associated with intrinsic sympathomimetic effects:

that the compound SCS 150 possesses adrenergic beta-blocking properties (about 70% of the beta-blocking properties of Pindolol) associated with intrinsic sympathomimetic effects;

that the compound SCS 151 has sympathomimetic characteristics;

that the compound SCS 152 possesses a certain beta-blocking effect.

These tests have been carried out on dogs (of both sexes) of weight comprised between 10 and 25 kg. These dogs were anesthetised by an injection of Pentobarbital (0.1 ml/kg of a 6% solution) and Chloralose (80 mg/kg). The blood pressure was recorded by means of a catheter inserted into the tibial artery and connected to a pressure cell, this pressure being recorded on a Beckman dynograph at the same time as an electrocardiogram; the latter enables the heart rhythm and the heart rate to be checked, integrated by a cardiotachometer.

The blood pressure and the electrocardiogram were first followed for five minutes. Then an isoproterenol solution was perfused into a cephalic vein, at the rate of 0.2 mcg/kg/min, namely 1 ml/min. After fiveperfusing for five minutes, the heart reached a tachycardiac level. At this moment, another perfusion was connected (into the cephalic vein of the other paw) of a Pindolol solution or of the product under study. The compounds of the invention was solubilized in 4 ml of DMF. The volume necessary for the perfusion was obtained by completing it with a 25% DMF solution in distilled water. All the products were injected at the rate of 25 mcg/kg/min. The The extent to which the products were capable of antagonising the cardio-acceleration on the one hand and the hypotension on the other hand was examined.

After 35 minutes of perfusion, the isoprenaline injection was stopped. The Pindolol perfusion or that of the compound under study was interrupted after 40 minutes. In this way, the total dose of 750 mcg of product was introduced into the blood flow during the isoprenaline perfusion and it is possible, on the cessation of the latter, to demonstrate possible sympathomimetic activity.

Tests on isolated bronchi and on isolated atria enabled the observation to be made that S.C.S. 149 had beta 1 blocking activity of competitive type at the cardiac level and of the competitive type at the bronchial elevel.

As for its toxicity, for the determination of which experiments were carried out on two animal species, namely the rat of the OFA strain and the mouse of the OF1 strain, by two routes of administration namely the oral route and the intravenous route, the results obtained were as follows:

ACUTE TOXICITY OF THE S.C.S. 149 PRODUCT ADMINISTERED BY THE ORAL ROUTE IN THE RAT

Oral Route

Death occured within 48 hours after the treatment.

| SPECIES - SEX | LD 50 (mg/kg) | 95% CONFIDENCE LIMITS |
| --- | --- | --- |
| Male rats | 3332.7 | 2788.8–3876.6 |
| Female rats | 2932.6 | 2453.6–3411.5 |

ACUTE TOXICITY OF THE PRODUCT S.C.S. 149 A ADMINISTERED BY THE ORAL ROUTE IN THE MOUSE

Oral Route

Death took place within 48 hours after treatment

| SPECIES - SEX | LD 50 (mg/kg) | 95% CONFIDENCE LIMITS |
| --- | --- | --- |
| Male mice | 560.13 | 501.8–625.2 |
| Female mice | 604.81 | 539.6–669.9 |

ACUTE TOXICITY OF THE PRODUCT S.C.S. 149 ADMINISTERED BY THE INTRAVENOUS ROUTE IN THE MOUSE

Intravenous Route

LD 50 48 hours after treatment.

| SPECIES - SEX | LD 50 (mg/kg) | 95% CONFIDENCE LIMITS |
| --- | --- | --- |
| Male mice | 37.25 | 33.7–40.7 |
| Female mice | 38.81 | 35.8–42.0 |

ACUTE TOXICITY OF THE PRODUCT S.C.S. 149 ADMINISTERED BY THE INTRAVENOUS ROUTE IN THE RAT

Intravenous Route

Death took place within 48 hours after administration of the product.

| SPECIES - SEX | LD 50 (mg/kg) | 95% CONFIDENCE LIMITS |
| --- | --- | --- |
| Male rats | 35.31 | 33.5–37.1 |
| Female rats | 40.37 | 39.8–42.9 |

ACUTE TOXICITY OF THE S.C.S. 149 PRODUCT ADMINISTERED BY THE INTRAVENOUS ROUTE IN THE MOUSE

Intravenous Route

LD 50 14 days after treatment.

| SPECIES - SEX | LD 50 (mg/kg) | 95% CONFIDENCE LIMITS |
| --- | --- | --- |
| Male mice | 37.25 | 33.7–40.7 |
| Female mice | 38.15 | 35.2–41.2 |

The product was solubilized, for oral administration, in 2% CMC in water; the volume administered was 25 ml/kg in the mouse and 5 ml/kg in the rat for the dose of 1 g/kg, 10 ml/kg for 2 g/kg and 20 ml/kg for 3.5 and 5 g/kg.

The product was administered by oesophagal intubation.

For the intravenous route, the product was solubilized in:

sterile water in the mouse

PEG 400+sterile water ($\frac{1}{3}+\frac{2}{3}$) in the rat.

The volume administered was:

1.25 ml/kg in the rat 12.5 ml/kg in the mouse.

The product was injected at the level of the caudal vein. Before administration of the product, the animals were kept fasting for 16 to 17 hours.

Also, toxicological tests have been carried out on 32 dogs (of both sexes) and 160 rats (of both sexes) for six months and have shown that S.C.S. 149 may be tolerated by the rats at a maximum daily dose of 500 mg/kg and by the dogs at a maximum daily dose of 100 mg/kg.

For administration to man, the posology and the presentation of the medicament were those currently known for the medicaments of the class of propanolols used for the treatment of high blood pressure, ischemic diseases of the heart and rhythmic disorders of the latter. These dosages are, for example, 5 to 20 mg/day, and the form was that of tablets.

Pharmacological tests have shown also that:

the compounds SCS 128 and 131 constituted, at suitably relatively high doses (of the order of 50 mg), cardiac stimulants.

It goes without saying that the present invention has been described here purely by way of indication and in only non-limiting manner and that any useful modification thereof could be introduced without departing from its scope as defined by the following claims.

We claim:

1. An acylated guanidine corresponding to the general formula:

$$R_1-O-CH_2-\underset{OH}{\underset{|}{CH}}-CH_2-\underset{R_2}{\underset{|}{N}}-\underset{NH}{\underset{||}{C}}-\underset{H}{\underset{|}{N}}-COR_3$$

in which $R_1$ represents phenyl or naphthyl optionally substituted by a monovalent group of —Cl or lower alkyl; $R_2$ represents an alkyl, benzyl or cycloalkyl group and $R_3$ represents phenyl, phenoxy, benzyloxy or alkyloxy group.

2. A composition for obtaining beta-blocking effects for the treatment of arterial hypertension, ischemic diseases of heart and rhythmic disorders of the latter, comprising a compound according to claim 1 in an amount effective for such a purpose, and a pharmaceutically acceptable carrier.

3. A medicament according to claim 2 wherein said compound corresponds to the general formula:

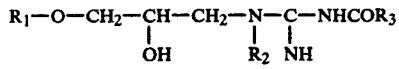

in which:

R₁ represents the o—ClC₆H₄— radical, R₂ represents the C₆H₁₁— radical and R₃ the C₂H₅—O— radical;

or R₁ represents the p—ClC₆H₄— radical, R₂ represents the C₆H₁₁— radical and R₃ the C₂H₅—O— radical;

or R₁ represents the p—ClC₆H₄— radical, R₂ represents the (CH₃)₂—CH— radical and R₃ represents the C₂H₅—O radical;

or R₁ represents the o—CH₃C₆H₄— radical, R₂ represents the (CH₃)₂CH— radical and R₃ represents the C₆H₅— radical;

or R₁ represents the o—CH₃C₆H₄— radical, R₂ represents the (CH₃)₂CH radical and R₃ the C₂H₅—O— radical;

or R₁ represents the o—CH₃C₆H₄— radical, R₂ represents the C₆H₁₁— radical and R₃ the C₂H₅—O— radical;

or again R₁ represents the p—CH₃C₆H₄— radical, R₂ represents the (CH₃)₂CH— radical and R₃ represents the C₂H₅—O— radical.

4. Method of treating human or animals to obtain beta-blocking effects for arterial hypertension, ischemic diseases of the heart and rhythmic disorders of the latter, by administrating to the subject a medicament comprising a compound according to claim 1.

* * * * *